(12) United States Patent
McNealy et al.

(10) Patent No.: US 7,706,988 B2
(45) Date of Patent: Apr. 27, 2010

(54) METHOD FOR IMPROVED CRACK DETECTION AND DISCRIMINATION USING CIRCUMFERENTIAL MAGNETIC FLUX LEAKAGE

(75) Inventors: Richard Clark McNealy, Houston, TX (US); Ming Gao, Houston, TX (US)

(73) Assignee: Blade Energy Partners, Inc., Frisco, TX (US)

( * ) Notice: Subject to any disclaimer, the term of this patent is extended or adjusted under 35 U.S.C. 154(b) by 0 days.

(21) Appl. No.: 12/075,903

(22) Filed: Mar. 14, 2008

(65) Prior Publication Data
US 2009/0234590 A1    Sep. 17, 2009

(51) Int. Cl.
G06F 19/00 (2006.01)
G01N 27/00 (2006.01)

(52) U.S. Cl. .......... 702/51; 702/35; 324/220; 324/228; 73/623; 73/643

(58) Field of Classification Search ......... 702/35, 702/51, 181; 324/220, 228, 238; 73/623, 73/643
See application file for complete search history.

(56) References Cited

U.S. PATENT DOCUMENTS

| | | | |
|---|---|---|---|
| 4,292,589 A | 9/1981 | Bonner | |
| 4,602,212 A | 7/1986 | Hiroshima et al. | |
| 6,037,767 A | 3/2000 | Crescenzo et al. | |
| 6,847,207 B1 | 1/2005 | Veach et al. | |
| 2001/0017541 A1 | 8/2001 | Kwun et al. | |
| 2001/0022514 A1 | 9/2001 | Light et al. | |
| 2001/0029989 A1 | 10/2001 | Paz | |
| 2003/0169065 A1* | 9/2003 | Eriguchi et al. | 324/765 |
| 2003/0198374 A1 | 10/2003 | Hagene et al. | |
| 2004/0040389 A1 | 3/2004 | Buttle | |
| 2004/0189289 A1 | 9/2004 | Atherton | |
| 2004/0217759 A1 | 11/2004 | Burkhardt et al. | |
| 2005/0072237 A1 | 4/2005 | Paige et al. | |
| 2005/0217394 A1 | 10/2005 | Langley et al. | |
| 2006/0025937 A1* | 2/2006 | Gao et al. | 702/35 |
| 2006/0076951 A1 | 4/2006 | Nestleroth et al. | |
| 2006/0164091 A1 | 7/2006 | Nestleroth et al. | |
| 2006/0202700 A1 | 9/2006 | Barolak et al. | |
| 2007/0120559 A1 | 5/2007 | Plotnikov et al. | |
| 2007/0222436 A1 | 9/2007 | Gao et al. | |
| 2008/0092672 A1 | 4/2008 | Gibson et al. | |

* cited by examiner

*Primary Examiner*—Bryan Bui
(74) *Attorney, Agent, or Firm*—Jeffrey L. Wendt

(57) ABSTRACT

A method of predicting at least one physical change in crack geometry of a crack in a pipeline based on in-line inspection operating pressure is presented. In one method, a first test on a pipeline is performed at a first pressure, which obtains a first set of test data. A second test is performed on the pipeline at a second pressure, obtaining a second set of test data. The first and second sets of test data are compared for any difference. A run comparison software processing device may be employed. In other methods, finite element analysis of crack-like dimensions is performed to predict Crack Mouth Opening Displacement (CMOD) for a given set of crack dimensions for a surface-breaking crack and inline pipe inspection operating run pressure. Another method predicts probability of detection of a crack associated with a given CMOD as a function of pressure in successive inspections.

20 Claims, 6 Drawing Sheets

METHOD FOR IMPROVED CRACK DETECTION AND DISCRIMINATION USING CIRCUMFERENTIAL MAGNETIC FLUX LEAKAGE

BACKGROUND

This disclosure relates to a method for improving the probability of discrimination of crack-like features from the numerous magnetic flux leakage signals routinely detected by in-line pipeline inspection (ILI) tools such as circumferential magnetization flux leakage (MFL) technology. One problem routinely encountered in application of MFL methods is discrimination of cracks and crack-like features, such as due to stress-corrosion cracking (SCC) from pipe geometric features, such as manufacturing or mill defects. While methods of using MFL ILI technology exists (such as disclosed in Published U.S. Pat. Appln. No. 20070222436, discussed below), the reliability of the discrimination by known methods may be improved.

Detection of a crack using MFL ILI tools requires disruption of an induced magnetic field for detection. MFL detects a high population of geometric features in addition to cracks, which negatively affects reliability. Moreover, flux leakage is impacted by stress level.

Published U.S. Pat. Appln. No. 20070222436 discloses a method for detecting stress corrosion cracking of pipelines, comprising the steps of: identifying pipeline locations and pipeline conditions that are amenable to inspection by a magnetic flux inline tool and by a TFI tool; performing two inspections on the pipeline, one inspection performed using the magnetic flux inline (MFL) tool and an other inspection performed using the TFI tool; aligning signal features resulting from the two inspections; identifying TFI signals occurring above an un-specified threshold; identifying MFL signals for a section of pipeline corresponding to the identified TFI signals; for the identified TFI signals, determining whether the MFL signals are below a second threshold level; designating the sections of the pipeline corresponding to identified TFI signals above the unspecified threshold and below the un-specified second threshold as a potential corrosion feature; identifying TFI signals that exceed a defined metal loss percentage; measuring a width and length of the signal features, and if the width and length of the signal feature exceed threshold crack width and length values, designating as a potential corrosion feature section of pipeline corresponding to the identified TFI signals.

While the methods disclosed in '436 may be useful in certain inspections, the methods do not describe a methodology for characterization of detection of cracks as a function of ILI run parameters. The '436 application also does not identify how much pressure differential is required between successive ILI runs to enable discrimination of crack-like features, or how to determine a pressure for a second inspection which reliably detects cracks but is not disruptive of the business of the pipeline owner or operator.

SUMMARY

The present disclosure describes a method for predicting physical changes in crack geometry based on ILI pressure and identifying the effect of such changes on the probability of detecting crack-like features using circumferential MFL ILI. These changes affect probability of detection, and application of the described method provides a basis for designing consecutive ILI runs whose data is aligned and compared to discriminate crack-like features from pipeline geometrical features. As used herein, "test" means circumferential MFL ILI test unless otherwise explicitly noted; "pressure" refers to internal pipeline pressure unless otherwise explicitly noted; and "pipeline" refers to transmission pipeline unless otherwise explicitly noted.

In one aspect, the present disclosure describes a method of predicting at least one physical change in crack geometry based on ILI pressure, the method comprising:
  a) performing a first test on a pipeline at a first pressure P1;
  b) obtaining a first set of test data on the pipeline at P1;
  c) performing a second test on the pipeline at a second pressure P2;
  d) obtaining a second set of test data on the pipeline at P2; and
  e) analyzing the first and second sets of test data for difference in feature signature at P1 vs. P2.

If a test data signal change is reported at a location along the pipeline, then the feature is a crack; if there is no change, there was no crack at the specified location in the pipeline. In some embodiments, the first pressure P1 is higher than, P2. In some embodiments, the analyzing of the first and second sets of test data for difference in feature signature at P1 vs. P2 is performed.

In another aspect, the present disclosure describes a method for using finite element analysis of crack-like dimensions in a pipeline to predict Crack Mouth Opening Displacement (CMOD) for a given set of crack dimensions for a surface-breaking crack and ILI operating run pressure, comprising:
  a) selecting yield strength (YS), diameter (D), and thickness (T) of a pipeline;
  b) selecting a pressure P;
  c) selecting a length (L), depth (d), and shape of a crack; and
  d) using the selections of (a)-(c) to perform finite element analysis (FEA) of the crack to predict CMOD as a function of d, L, YS, D, T and P.

In some embodiments, the method steps are repeated at at least two different values of YS, D, T, P, L, and d. In some embodiments, the selecting of YS, D, and T of a pipeline is for a hypothetical pipeline. In other embodiments, the selecting of YS, D, and T of a pipeline is for an existing pipeline. In some embodiments, the selecting of L, d and shape of crack is for a hypothetical crack. In other embodiments, the selecting of L, d, and shape of a crack is for an existing crack. In certain embodiments, combinations of hypothetical and existing pipeline and crack parameters may be used in the method to predict CMOD as a function of d, L, YS, D, T and P. For example, in certain embodiments the method to predict CMOD as a function of d, L, YS and P may be for a hypothetical crack and for an existing pipeline.

In another aspect, the present disclosure describes a method of predicting the probability of detection (POD) of a crack associated with a given CMOD as a function of pressure in successive ILI tests, the method comprising:
  a) selecting a MFL ILI tool having a given POD for a crack of a given dimension in a pipeline of given diameter, T, and YS;
  b) selecting a mathematical equation describing POD as a function of CMOD and at least one constant, the constant being a characteristic of the tool;
  c) determining the at least one constant by solving the mathematical equation;
  d) graphing POD as a function of CMOD at a given first pressure P1, L and d (as defined above); and e) recommending a first test at the first pressure P1 and a second test at a second pressure P2 allowing discrimination of crack-like features from geometric features in the pipeline.

In some embodiments, the determining of the second P allowing discrimination of crack-like features from geometric features in the pipeline is by generating a set of design curves as explained in the example provided herein. In some embodiments, the mathematical equation may have one, two, or more constants. In some embodiments, the mathematical equation has one constant. In other embodiments, the graphing of POD as a function of CMOD may be performed at other P, L and d. In some embodiments, the three POD zones are defined (low, moderate and high) based on tool specifications and empirical crack detection data. In certain embodiments, a low second P for the second detection run is recommended, as features at this low second P are in the low POD zone. In certain methods the POD and second P are validated by excavation data.

These aspects of the disclosure will be better understood with reference to the detailed description which follows.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION

The present disclosure describes a pipeline inspection method including running tests at two different pressures, comparing the results of the tests at the two different pressures. The present disclosure also describes how to select the test pressures (ILI run pressures) in order to increase the probability of detection of cracks.

Figure 1:
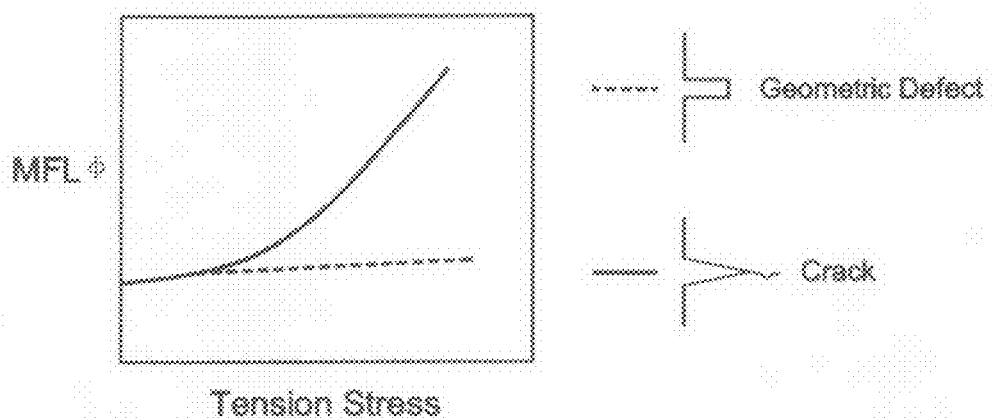
FIG. 1 is a prior art graph of magnetic flux leakage vs. pipe stress, providing a mechanistic understanding of the relationship between flux leakage and stress.

Referring to FIG. 1, FIG. 1 is a prior art schematic graph of magnetic flux leakage as a function of pipe stress, providing a mechanistic understanding of the relationship between flux leakage and tension stress. As illustrated in FIG. 1, at certain stress levels below a certain stress, a crack will not be discriminated from a geometric defect. The tension stress is typically produced by internal pressure fluid (gas or liquid) flowing through the pipeline.

Figure 2:
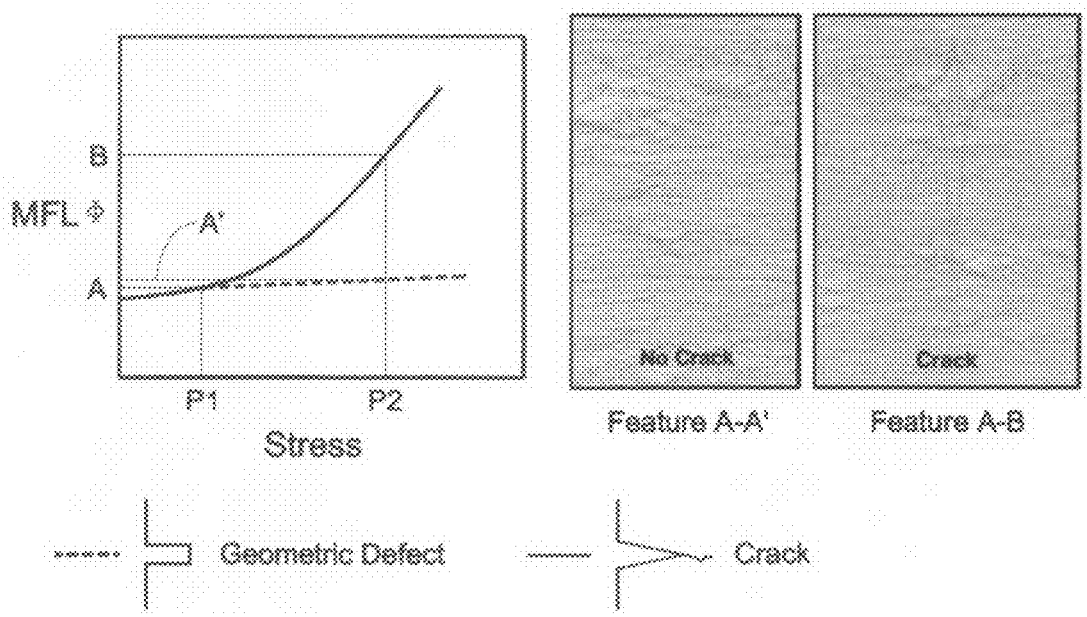
FIG. 2 illustrates graphically use of a method of the present disclosure to discriminate a crack from a geometric feature.

FIG. 2 illustrates graphically use of a method of the present disclosure to discriminate a crack from a geometric feature. Two inspection runs are designed, a first run at a first pressure P1 and a second test run at a second pressure P2. In certain methods of this disclosure, the first and second sets of test data are analyzed for difference in feature signal at P1 and P2. If a test data signal change is reported at a location along the pipeline, then the feature is a crack; if there is no change, there was no crack at the specified location in the pipeline. In some embodiments, the first pressure P1 is higher than P2. In some embodiments, the analyzing of the first and second sets of test data for difference in feature signature at P1 vs. P2 is performed. As illustrated in FIG. 2, the change in magnetic flux designated A-A' is representative of "no crack". While the change in magnetic flux designated A-B is representative of a detected crack.

Figure 3:
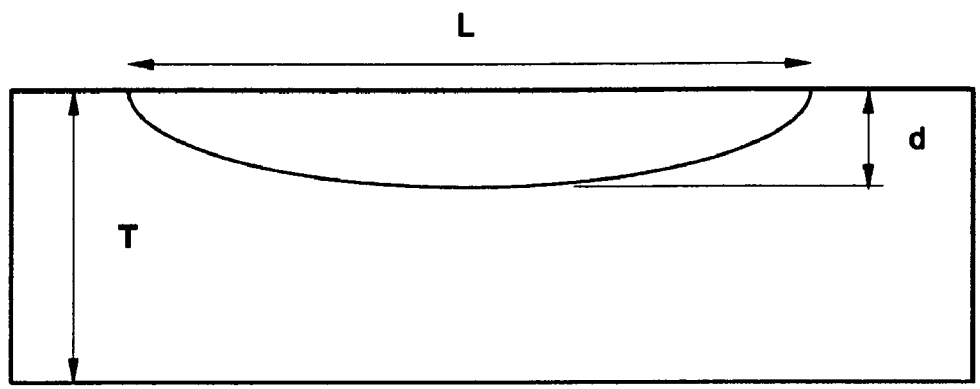
FIG. 3 illustrates parameters of a crack used in certain methods of the disclosure.

FIG. 3 illustrates parameters of a crack and pipeline used in certain methods of the disclosure. Crack length L and depth d, as well as pipeline thickness T are illustrated. The shape of the pipeline may be selected as cylindrical but that is not necessary to practicing the invention. In a finite element analysis, the grade of the pipeline is also used, which is reflected in the yield strength (YS) of the steel or other material making up the pipeline. As illustrated in FIG. 3, the crack is a "surface-breaking" crack, meaning that it opens to the outer surface of the pipeline. The shape of the crack may be any shape, including elliptical, circular, oval, or box-shaped. The depth d of the crack may range from about 1 to about 99% of the thickness T, or from about 10 to about 90%, or from about 20 to about 80%, or from about 30 to about 70%, or form about 40 to about 60%, or even about 50%. The length L of the crack may range from about 1 to about 12 inches or greater (about 2.54 cm to about 30.5 cm), or from about 1 to about 8 inches (2.54 cm to about 20.3 cm), or from about 1 to about 6 inches (2.54 cm to about 15.2 cm). The crack may be a single crack or a crack field. Internal pipeline pressures may range from about 200 psi to about 2000 psi (from about 1.4 MPa to about 14 MPa), or from about 300 psi to about 1800 psi (2.1 MPa to about 12.4 MPa), or about 400 psi to about 1500 psi (about 2.8 MPa to about 10.3 MPa), or from about 500 to about 1000 psi (3.4 MPa to about 6.9 MPa).

Figure 4:
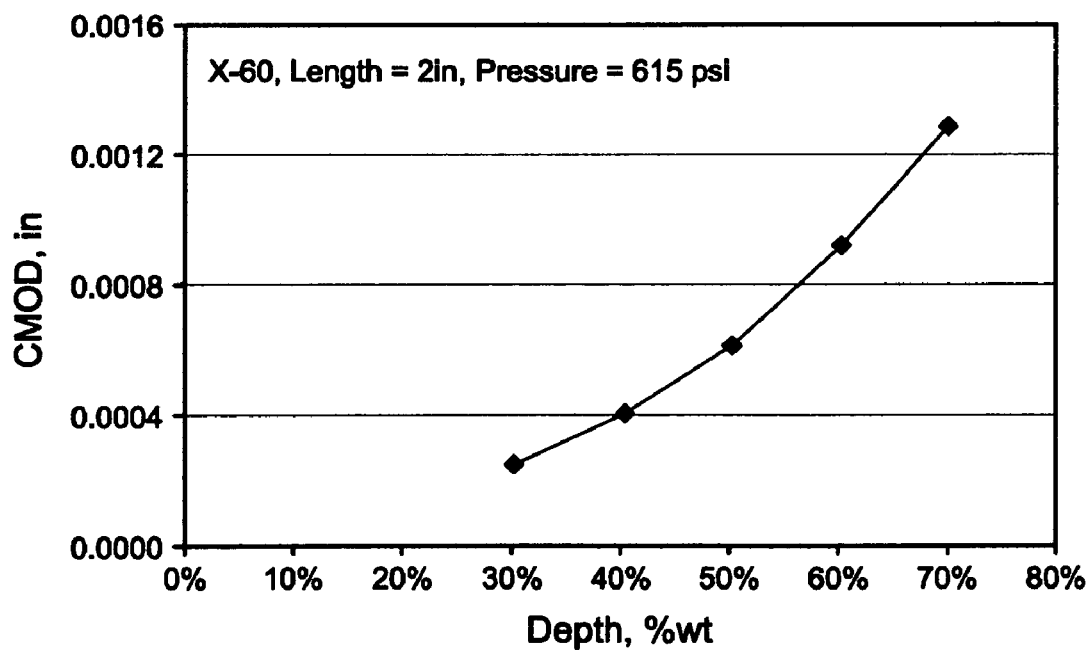
FIGS. 4-6 are graphs of CMOD as a function of crack depth expressed in percentage of wall thickness, CMOD as a function of length of a crack, and CMOD as a function of pipeline pressure.
Figure 5:
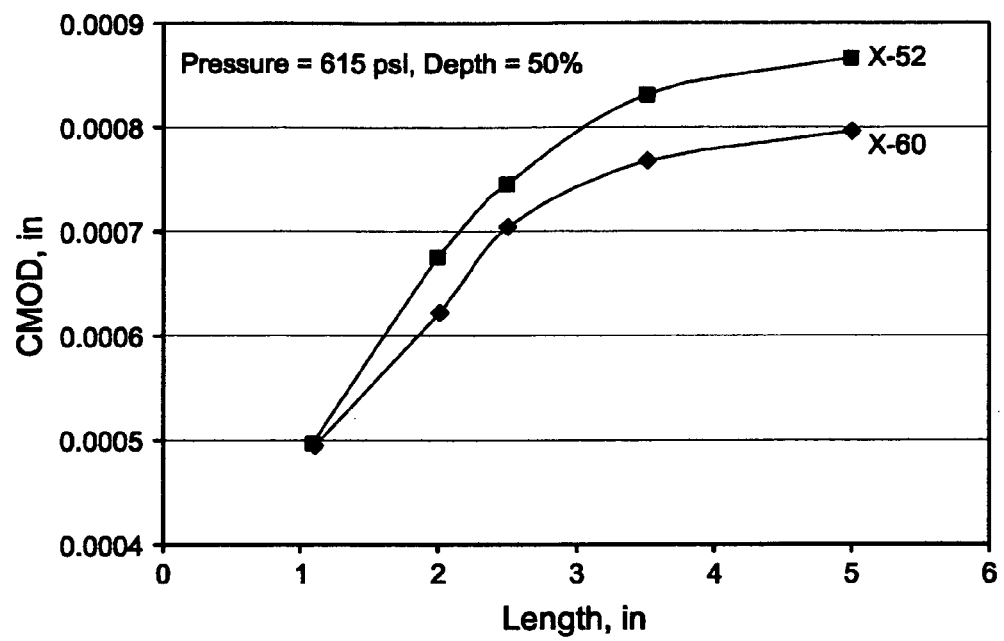
Figure 6:
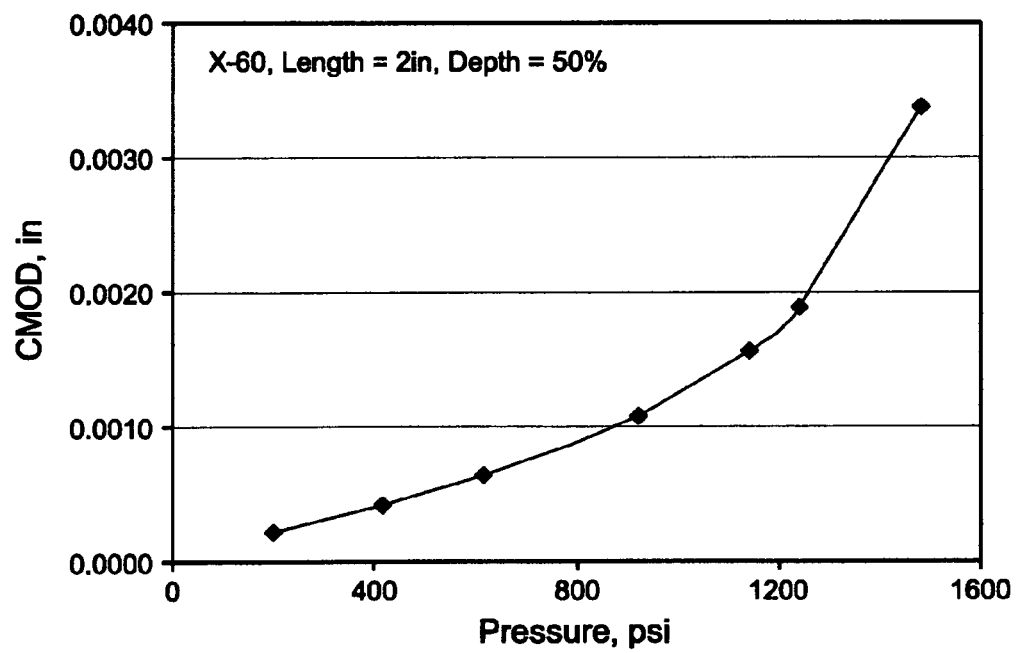

FIG. 4 is a graph of CMOD as a function of crack depth expressed in % wall thickness (but could also be expressed as absolute crack depth in inches or millimeters), for grade X-60 steel for a crack of length 2 inches (5.1 cm) and pressure of 615 psi (4.2 MPa). Generally, CMOD increases as a function of crack depth for this steel at this pressure and length of crack. FIG. 5 illustrates that for the same grade steel and pressure, at a fixed crack depth percentage of 50% of wall thickness, CMOD first increases as length of crack increases, then levels off after a crack length of about 3.5 inches (8.9 cm). Steel grade X-52 shows essentially the same shape of curve but slightly higher CMOD values. FIG. 6 illustrates CMOD as a function of pressure for grade X-60 steel, crack length of 2 inches (5.1 cm), crack depth percentage of 50%.

Figure 7:
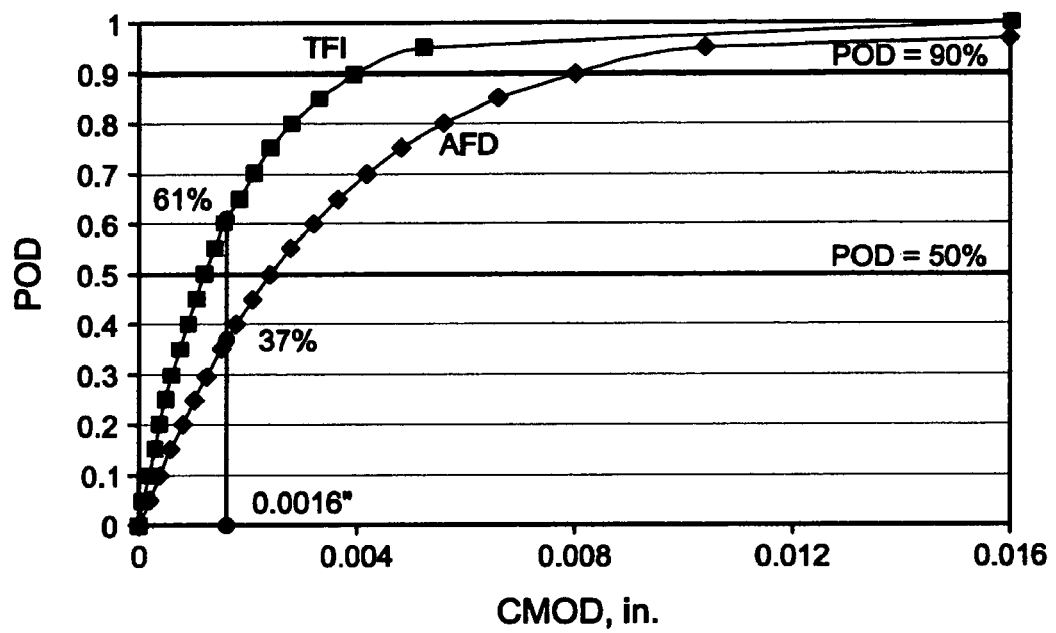
FIG. 7 is a graph of probability of detection (POD) as a function of CMOD for two known MFL inspection tools.
Figure 8:
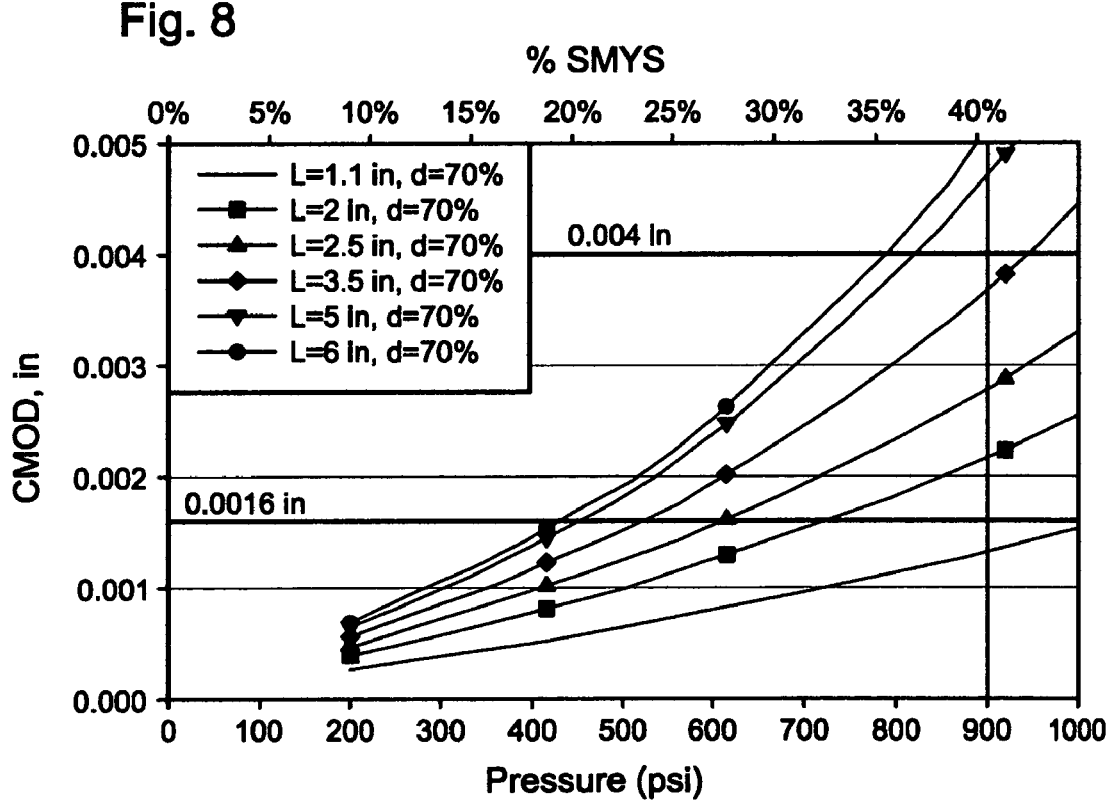
FIGS. 8-11 are graphs of CMOD as a function of test run pressure for X-60 grade steel at four different crack depths.
Figure 9:
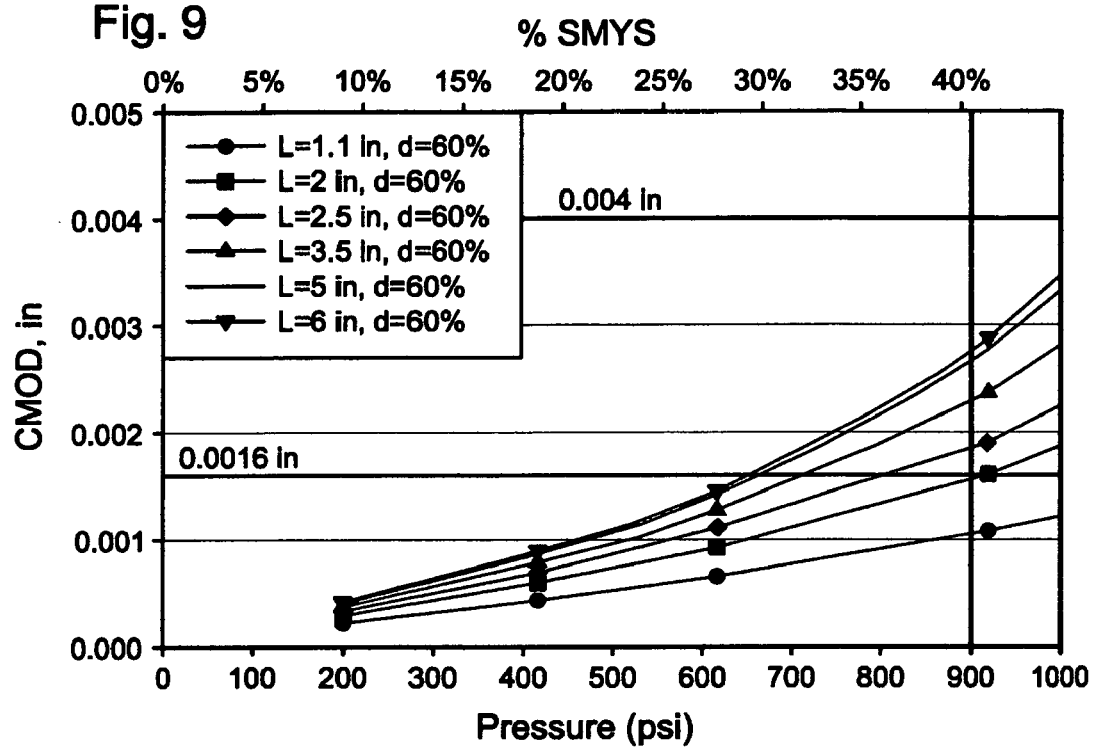
Figure 10:
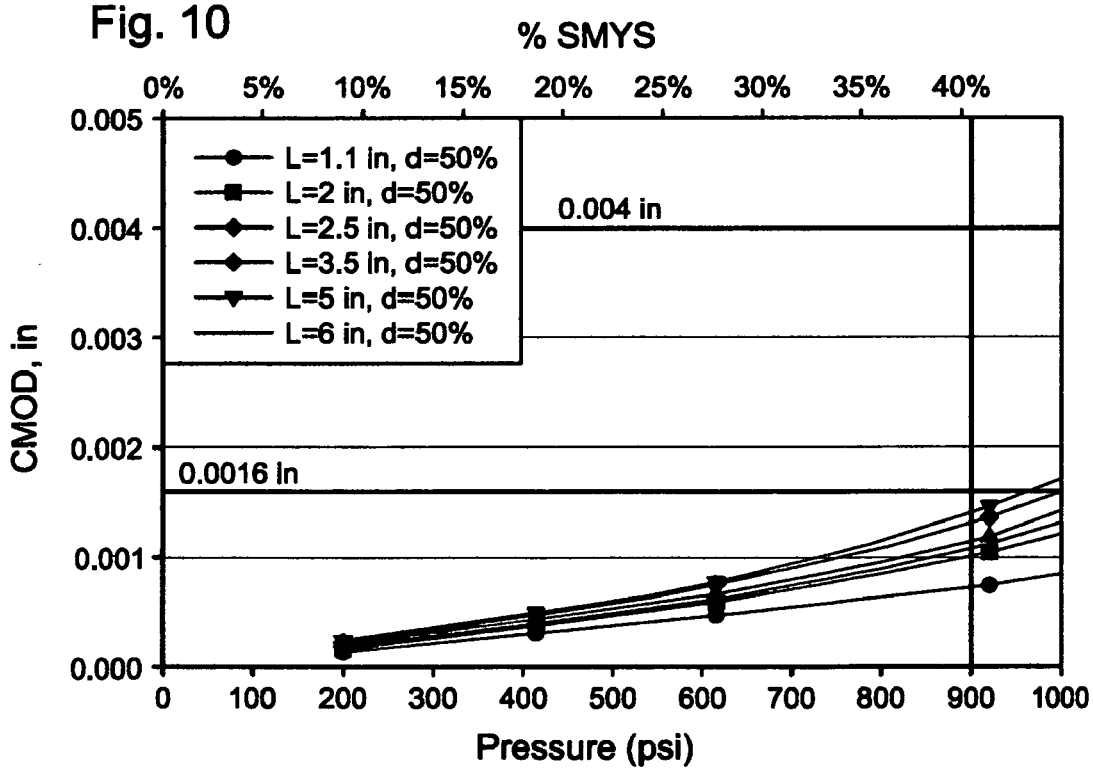
Figure 11:
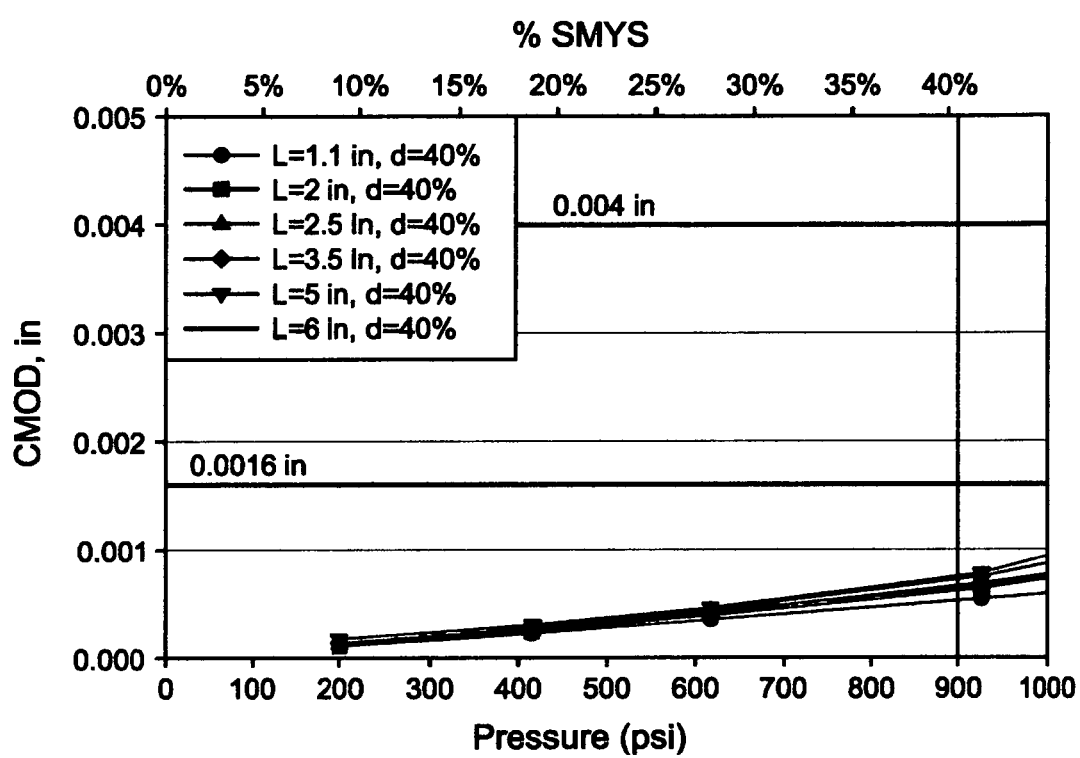

FIG. 7 is a graph of probability of detection (POD) as a function of CMOD for two known MFL inspection tools. These curves were obtained by assuming that the mathematical model for corrosion features suggested by Rodriguez III, E. S. et al., "Development of a General Failure Control System for Estimating the Reliability of Deteriorating Structures", *Corrosion*, Vol. 45, No. 3, pp. 193-206 (1989) is applied in this embodiment to MFL detection. The Rodriguez III et al. equation is as follows:

$$POD = 1 - e^{-qh} \quad (1)$$

where POD is probability of detection;
h is a defect size, for example crack depth; and
q is a constant that is characteristic of the overall power of the detection tool.

Because equation (1) contains only three unknowns, and two of the three unknowns are given by the tool manufacturer (for example, for a Rosen AFD tool, for 0.2 mm crack depth, POD is 90%; for a PII TFI tool, for a crack depth of 0.1 mm, POD is 90%), the constant q is easily determined. For the Rosen AFD tool, q is 23, and for the PII TFI tool, q is 11.5. This allows the curves of FIG. 7 to be developed for each tool. Note that three confidence levels may be defined: a high confidence zone (POD of 90% and greater, which is typically suggested by the pipeline operator, and is not changeable); a moderate confidence zone where POD ranges from about 90% to about 50% or lower; and a low confidence zone below POD of about 50%. These curves in turn allow generation of a family of design curves, such as illustrated in FIGS. 8-11.

It should be emphasized that Equation (1) is merely an example, and other equations could be used to provide even more rigorous results.

FIGS. 8-11 are graphs of CMOD as a function of test run pressure for X-60 grade steel at four different crack depths. These graphs indicate that the first inspection test pressure should be as high as possible, as indicated by the claimed method (model), for maximizing the POD (probability of detection) and the second inspection test pressure should be as low as possible for maximizing POI (probability of Identification), and that the pressure and CMOD should lie in the low POD zone.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A method of predicting at least one physical change in crack geometry based on ILI pressure, the method comprising:
    a) performing a first test on a pipeline at a first pressure P1;
    b) obtaining a first set of test data on the pipeline at P1;
    c) performing a second test on the pipeline at a second pressure P2;
    d) obtaining a second set of test data on the pipeline at P2; and
    e) analyzing the first and second sets of test data for difference in feature signature at P1 vs. P2,
    wherein the analyzing of the first and second sets of test data for difference in feature signature at P1 vs. P2 is performed using a run comparison software processing device.

2. The method according to claim 1, wherein the analyzing comprises determining if a test data signal change is reported at a location along the pipeline.

3. The method according to claim 2, wherein if there is a change, noting the change as a crack at the location.

4. The method according to claim 1, wherein the first pressure P1 is higher than P2.

5. A method for using finite element analysis of crack-like dimensions in a pipeline to predict Crack Mouth Opening Displacement (CMOD) for a given set of crack dimensions for an external and internal surface-breaking crack and ILI operating run pressure, comprising:
    a) selecting yield strength (YS), diameter (D), and thickness (T) of a pipeline;
    b) selecting a pressure P;
    c) selecting a length (L), depth (d), and shape of an external and internal surface breaking crack; and
    d) using the selections of (a)-(c) to perform finite element analysis (FEA) of the crack to predict CMOD as a function of d, L, YS, D, T and P employing a finite element analysis software processing device.

6. The method according to claim 5, wherein the method steps are repeated at at least two different values of YS, D, T, P, L, and d.

7. The method according to claim 5, wherein the selecting of YS, D, and T of the pipeline is for a hypothetical pipeline.

8. The method according to claim 5, wherein the selecting of YS, D, and T of the pipeline is for an existing pipeline.

9. The method according to claim 5, wherein the selecting of L, d and shape of the crack is for a hypothetical crack.

10. The method according to claim 5, wherein the selecting of L, d and shape of the crack is for an existing crack.

11. The method according to claim 5, wherein the method to predict CMOD as a function of d, L, YS, D, T and P is for a hypothetical crack and for an existing pipeline.

12. The method according to claim 5, wherein the method to predict CMOD as a function of d, L, YS, D, T and P is for a hypothetical pipeline and for an existing crack.

13. A method of predicting the probability of detection (POD) of a crack associated with a given CMOD as a function of pressure in successive ILI tests, the method comprising:
    a) selecting a MFL ILI tool having a given POD for a crack of a given dimension in a pipeline of given diameter (D), wall thickness (T), and yield strength (YS);
    b) selecting a mathematical equation describing POD as a function of CMOD and at least one constant, the constant being a characteristic of the tool;
    c) determining the at least one constant by solving the mathematical equation;
    d) graphing POD as a function of CMOD for a first test run at a given first pressure P1, L and d; and
    e) recommending a first test at the first pressure P1 and a second test at a second pressure P2 allowing discrimination of crack-like features from geometric features in the pipeline, wherein the first test comprises detecting crack-like features and the second test comprises discriminating crack-like features from geometric features in the pipeline by generating a set of design curves, the discriminating using a run comparison software processing device.

14. The method according to claim 13, wherein the mathematical equation has at least two constants.

15. The method according to claim 13, wherein the mathematical equation has one constant.

16. The method according to claim 13, wherein the graphing of POD as a function of CMOD is performed at another set of P, L, D, T, YS and d.

17. The method according to claim 13, wherein the graphing of POD as a function of CMOD is performed for a second tool on the same graph.

18. The method according to claim 13, wherein three POD zones are defined (low, moderate and high) based on tool specifications and empirical crack detection data.

19. The method according to claim 18, wherein the recommending of the second test at the second pressure $P_2$ comprises recommending a pressure lower than P1 for the second test, wherein features at this low second P2 are in the low POD zone.

20. The method according to claim 13, wherein the POD and second pressure P2 are validated by actual measurements after excavating the pipeline in the vicinity of the crack.

* * * * *